United States Patent [19]

Asai et al.

[11] Patent Number: 5,741,487

[45] Date of Patent: Apr. 21, 1998

[54] MUTANASE-CONTAINING ORAL COMPOSITIONS

[75] Inventors: Yoshio Asai; Motoyasu Ohdera; Hiromitsu Kigawa; Isao Shimotsuura; Yoshiko Yokobori; Masanori Hirano; Koji Shibuya, all of Tokyo, Japan

[73] Assignee: Lion Corporation, Tokyo, Japan

[21] Appl. No.: 806,626

[22] Filed: Feb. 26, 1997

[30] Foreign Application Priority Data

May 16, 1996 [JP] Japan .................................. 8-146613

[51] Int. Cl.⁶ .................................................. A61K 38/47
[52] U.S. Cl. ........................................................ 424/94.61
[58] Field of Search ........................................... 424/94.61

[56] References Cited

U.S. PATENT DOCUMENTS 5,306,639  4/1994  Matsushiro ............................ 435/320.1

FOREIGN PATENT DOCUMENTS

8308558A   11/1996   Japan .
8308559A   11/1996   Japan .
9037773A   2/1997    Japan .

Primary Examiner—Raymond Henley, III
Attorney, Agent, or Firm—Birch, Stewart, Kolasch & Birch, LLP

[57] ABSTRACT

An oral composition contains mutanase prepared from a culture which is obtained by cultivating a mutanase-producing microorganism belonging to the genus Bacillus having negative protease producibility. The oral composition is effective for suppressing dental plaque formation while the mutanase possesses commercially acceptable stability in the oral composition.

9 Claims, 6 Drawing Sheets

MUTANASE-CONTAINING ORAL COMPOSITIONS

BACKGROUND OF THE INVENTION

1. Field of the Invention

This invention relates to an oral composition comprising mutanase.

2. Prior Art

It is generally believed that dental caries is caused by bacteria in the oral cavity such as *Streptococcus mutans* and *Streptococcus sobrinus* which produce dental plaque composed of insoluble glucans. Bacteria produce acids in dental plaque to demineralize teeth, causing dental caries.

One effective means for removing the dental plaque is to use enzymes capable of decomposing insoluble glucans which produce dental plaque. The insoluble glucan molecules are mainly composed of α-1,6-glucosidic links and α-1,3-glucosidic links in a complex manner. It is known in the art that dextranase capable of cleaving α-1,6 links and mutanase capable of cleaving α-1,3 links are effective for suppressing dental plaque formation. Oral compositions having either dextranase or mutanase are known as disclosed in Japanese Patent Nos. 782154 and 1055365.

Dextranase and mutanase attack dental plaque at different sites. JP-A 165312/1982 discloses that combined use of dextranase and mutanase achieves more effective suppression of dental plaque formation than individual use.

However, only a limited number of mutanases are commercially available in the market by far now. No mutanase-containing oral products such as dentifrice are available in the market. This is because commercial mutanases currently available lack stability such as thermal stability and stability in composition although such stability is necessary to blend in oral compositions such as dentifrice and mouthwash. Few commercial products of stable mutanase are in steady supply.

SUMMARY OF THE INVENTION

Therefore, an object of the present invention is to provide a novel and improved oral composition which has mutanase formulated in a stable manner and is effective for suppressing dental plaque formation and removing dental plaque.

The present invention provides an oral composition comprising mutanase prepared from a culture which is obtained by cultivating a mutanase-producing microorganism belonging to the genus Bacillus having negative protease producibility.

In another aspect, the present invention provides an oral composition comprising mutanase having the following physicochemical properties (1) to (9).

(1) action: an ability to cleave α-1,3-glucosidic links of mutan, (2) substrate specificity: an ability to effectively decompose mutan, (3) optimum pH: pH 4 to 4.5 when reacting on a mutan substrate at 35° C. for 10 minutes, (4) pH range for stability: pH 4 to 10 when kept at 25° C. for 24 hours, (5) optimum temperature: 50° to 65° C. when reacted at pH 5 with mutan as a substrate, (6) thermal stability: enzyme activity remains stable below 50° C. after incubation at pH 5 for 10 minutes, (7) effect of metal ions: mercury and silver show inhibitory effect on a mutan substrate, (8) effect of inhibitors: p-chloromercurybenzoic acid shows inhibitory effect on a mutan substrate, and (9) molecular weight: about 140,000 to about 160,000 as determined by SDS-polyacrylamide gel electrophoresis.

The oral composition of the invention is highly effective for preventing dental plaque since mutanase is effective for suppressing dental caries formation and removing dental plaque.

Combined use of dextranase and mutanase is more effective for suppressing dental plaque formation.

DESCRIPTION OF THE PREFERRED EMBODIMENTS

Briefly stated, the invention provides an oral composition comprising specific mutanase.

The oral composition may be prepared as dentifrice such as toothpaste, tooth powder and liquid dentifrice, mouthwashes, mouth rinse, gingival massage cream, oral paste, gargling tablets, denture cleaners, chewing gum, and troche and in solid, liquid, and paste forms.

The mutanase used herein is mutanase prepared from a culture which is obtained by cultivating a mutanase-producing microorganism belonging to the genus Bacillus having negative protease producibility. Blending this type of mutanase provides an oral composition with abilities to effectively decompose plaque and effectively prevent caries while this type of mutanase remains stable in the oral composition.

The mutanase-producing microorganisms are preferably negative in gram-staining. Mutanase-producing microorganisms are weakly positive and readily decolored in gram-staining are also acceptable. Such mutanase-producing microorganisms include first, second and third mutanase-producing microorganisms as shown below although they are not limited to these examples. Any of mutanase-producing microorganisms satisfying the above-mentioned properties is useful.

The first to third mutanase-producing microorganisms are isolated from soil. They belong to the genus Bacillus and have negative protease producibility.

The first and second mutanase-producing microorganisms are further characterized by gram-staining. Both show negative results. The growth of the first mutanase-producing microorganism is observed in the range of pH 5 to 8.5. For the second mutanase-producing microorganism, the growth range is from pH 5 to 7.5. They are discriminatable from other mutanase-producing microorganisms in that they produce mutanase having the above-mentioned physicochemical properties (1) to (9). These strains have the following microbiological properties. The following properties are common for the first and second mutanase-producing microorganisms unless otherwise stated.

It is noted that with respect to microbiological properties and identification, reference is made to Bergey's Manual of Systematic Bacteriology (1984) and the Genus Bacillus (1973).

A. Morphological properties

When microorganisms are cultivated on a nutrient agar at 40° C. for 2 days, the following morphological characteristics are observed.

(A-1) Shape and size of cells: rods, size 0.6 to 1 μm×3 to 4 μm (A-2) Pleomorphism: none (A-3) Motility: peritrichous flagella, motile (A-4) Spore: There are formed spores which are ellipsoidal in shape and 1 μm×1.2 to 1.7 μm in size. Their positions are center to terminal. Sporangium is distended.

(A-5) Gram-stain: negative (A-6) Acid fastness: negative

B. Cultural properties (B-1) Nutrient agar plate culture: Circular, flat and entire colonies are formed. The first mutanase-producing microorganism forms milky white or cream colored colonies at the central region and semi-transparent milky white or cream colored colonies at the peripheral region. The second mutanase-producing microorganism forms milky white colonies at the central region and semi-transparent milky white colonies at the outer peripheral region. They both are glossy and smooth.

(B-2) Nutrient agar slant culture: grow in a strip or broad strip form white or cream colored colonies.

(B-3) Nutrient liquid culture: grow, but not form pellicle.

(B-4) Gelatin stab culture: grow, but not liquefied.

(B-5) Litmus milk: not decolored, not liquefied.

C. Physiological properties (C-1) Reduction of nitrate: negative (C-2) Denitrification: negative (C-3) MR test: negative (C-4) VP test: negative (C-5) VP broth pH after cultivation: 6.37 with the first mutanase-producing microorganism, 6.98 with the second mutanase-producing microorganism (C-6) indole formation: not detected (C-7) Hydrogen sulfide formation: not detected (C-8) Starch hydrolysis: positive (C-9) Utilization of citric acid: do not utilize in Simmons' medium, do not utilize in Christensen's medium.

(C-10) Utilization of inorganic nitrogen sources: utilize nitrates, utilize ammonium salts.

(C-11) Pigment formation: negative (C-12) Urease: negative (C-13) Oxidase: the first mutanase-producing microorganism is positive, the second mutanase-producing microorganism is very weak (C-14) Catalase: positive (C-15) Growth range:
the first mutanase-producing microorganism
pH range 5 to 8.5
temperature range 25° to 60° C.
the second mutanase-producing microorganism
pH range 5 to 7.5
temperature range 25° to 53° C.

(C-16) Behavior to oxygen: aerobic (C-17) O—F test: aerobic decomposition (C-18) Acid and gas formation from saccharides: As shown in Table 1 wherein "+" means that microorganisms form acid or gas and "−" means that microorganisms do not form acid or gas.

TABLE 1

| Saccharide | Acid formation | Gas formation |
|---|---|---|
| L-arabinose | + | − |
| D-xylose | + | − |
| D-glucose | + | − |
| D-mannose | + | − |
| D-fructose | + | − |
| D-galactose | + | − |
| Maltose | + | − |
| Sucrose | + | − |
| Lactose | + | − |
| Trehalose | + | − |
| D-sorbitol | + | − |
| D-mannitol | + | − |
| Inositol | + | − |
| Glycerin | + | − |
| Starch | + | − |

D. Other properties (D-1) Resistance to sodium chloride: grow in nutrient agar in the presence of 2% sodium chloride, but do not grow in the presence of 5% sodium chloride (D-2) Anaerobic growth: negative (D-3) Casein decomposition: negative (D-4) Utilization of propionates: negative (D-5) Growth at pH 6.8: positive (D-6) Growth at pH 5.7: positive (D-7) Crystal formation: negative (D-8) Protease production: negative The third mutanase-producing microorganism is further characterized in that it is gram-stained positive and readily decolored. It is discriminatable from other mutanase-producing microorganisms in that it produces mutanase having the above-mentioned physicochemical properties (1) to (9). Its strain has the following microbiological properties.

A. Morphological properties

When microorganisms are cultivated on nutrient agar at 30° C. for 2 days, the following morphological characteristics are observed.

(A-1) Shape and size of cells: rods, size 1 to2 μm×4 to 6 μm (A-2) Pleomorphism: none (A-3) Motility: peritrichous flagella, motile (A-4) Spore: There are formed spores which are ellipsoidal in shape and 1 to 1.5 μm×2 to 3 μm in size. Their positions are central to terminal. Sporangium is distended.

(A-5) Gram-stain: weakly positive and readily decolored (A-6) Acid fastness: negative

B. Cultural properties (B-1) Nutrient agar plate culture: Circular, flat and entire colonies are formed. Colonies are white and not glossy.

(B-2) Nutrient agar slant culture: grow in a strip or broad strip, form white or cream colored colonies.

(B-3) Nutrient liquid culture: grow, but not form pellicle.

(B-4) Gelatin stab culture: grow, but not liquefied.

(B-5) Litmus milk: not decolored, neither liquefied nor coagulated.

C. Physiological properties (C-1) Reduction of nitrate: positive (C-2) Denitrification: negative (C-3) MR test: negative (C-4) VP test: negative (C-5) VP broth pH after cultivation: 5.8

(C-6) Indole formation: not detected (C-7) Hydrogen sulfide formation: not detected (C-8) Starch hydrolysis: very weak (C-9) Utilization of citric acid: do not utilize in Simmons' medium, do not utilize in Christensen's medium.

(C-10) Utilization of inorganic nitrogen sources: slightly utilize nitrates, utilize ammonium salts.

(C-11) Pigment formation: negative (C-12) Urease: negative (C-13) Oxidase: positive (C-14) Catalase: negative (C-15) Growth range:

pH range 6 to 8 temperature range 20° to 33° C.

(C-16) Behavior to oxygen: aerobic (C-17) O—F test: aerobic decomposition (C-18) Acid and gas formation from saccharides: As shown in Table 2 wherein "+" means that microorganisms form acid or gas, "−" means that microorganisms do not form acid or gas, and "±" means weak formation.

TABLE 2

| Saccharide | Acid formation | Gas formation |
| --- | --- | --- |
| L-arabinose | − | − |
| D-xylose | ± | − |
| D-glucose | + | − |
| D-mannose | ± | − |
| D-fructose | − | − |
| D-galactose | − | − |
| Maltose | − | − |
| Sucrose | + | − |
| Lactose | − | − |
| Trehalose | − | − |
| D-sorbitol | + | − |
| D-mannitol | + | − |
| Inositol | − | − |
| Glycerin | − | − |
| Starch | + | − |

D. Other properties (D-1) Resistance to sodium chloride: do not grow in nutrient agar in the presence of 2% sodium chloride (D-2) Anaerobic growth: negative (D-3) Casein decomposition: negative (D-4) Utilization of propionates: negative (D-5) Growth at pH 6.8: positive (D-6) Growth at pH 5.7: positive (D-7) Crystal formation: negative (D-8) Protease production: negative (D-9) GC content: 56%

Described below is the difference between strains of the above-mentioned mutanase-producing microorganisms and strains of well-known mutanase-producing microorganisms. The well-known mutanase-producing microorganisms include those belonging to the genus Pseudomonas, genus Flavobacterium, genus Bacillus, genus Streptomyces, genus Trichoderma and genus Aspergillus.

First, reference is made to a strain of *Bacillus circulans* BC-8 belonging to the same genus Bacillus as the above-mentioned mutanase-producing microorganisms (see JP-A 301788/1988). The first and second mutanase-producing microorganisms show negative in gram-staining whereas BC-8 strain is positive. The first and second mutanase-producing microorganisms form spores at central to terminal positions whereas BC-8 strain forms spores at a terminal position. The first and second mutanase-producing microorganisms show negative growth in 5% NaCl whereas BC-8 strain is positive. The first and second mutanase-producing microorganisms are positive in acid production from L-arabinose whereas BC-8 is negative. The first and second mutanase-producing microorganisms are positive in acid production from D-xylose whereas BC-8 strain is negative. The first and second mutanase-producing microorganisms are positive in growth at 45° C. whereas BC-8 strain is negative.

The third mutanase-producing microorganism is weakly positive and readily decolored in gram-staining whereas BC-8 strain is positive. The third mutanase-producing microorganism is motile and forms spores at central to terminal positions whereas BC-8 strain is not motile and forms spores at a terminal position. The third mutanase-producing microorganism is negative for catalase activity and positive in nitrate reduction whereas BC-8 strain is positive for catalase activity and negative in nitrate reduction. The third mutanase-producing microorganism shows negative growth in 5% NaCl whereas BC-8 strain is positive. The third mutanase-producing microorganisms is weakly positive in acid production from D-xylose whereas BC-8 strain is negative. The third mutanase-producing microorganism has a GC content of 56% whereas BC-8 strain has a GC content of 49.5%.

Next a comparison is made with a strain of *Bacillus circulans* FERM-P4765 belonging to the same genus Bacillus as the above-mentioned first to third mutanase-producing microorganisms (see JP-A 88693/1980) although its microbiological properties are unknown. The first mutanase-producing microorganism produces mutanase having a molecular weight of about 150,000, an optimum temperature of 60° C. and optimum pH 4 and the second mutanase-producing microorganism produces mutanase having a molecular weight of about 140,000, an optimum temperature of 65° C. and optimum pH 4.5 whereas FERM-P4765 strain produces mutanase having a molecular weight of more than about 70,000, an optimum temperature of 30° to 40° C. and optimum pH 6.2 to 6.7. Then the first and second mutanase-producing microorganisms are discriminatable from FERM-P4765 strain.

The third mutanase-producing microorganism produces mutanase having a molecular weight of about 160,000, an optimum temperature of 50° C. and optimum pH 4.5 whereas FERM-P4765 strain produces mutanase having a molecular weight of more than about 70,000, an optimum temperature of 30° to 40° C. and optimum pH 6.2 to 6.7. Then the third mutanase-producing microorganism is discriminatable from FERM-P4765 strain.

Moreover, mutanase-producing microorganisms described in JP-A 34980/1977, belong to the genus Streptomyces, mutanase-producing microorganisms described in JP-A 145583/1975 belong to the genus Flavobacterium, mutanase-producing microorganisms described in JP-A 9743/1972 are *Trichoderma hargianum*, *Penicillium lilacinum*, *Penicillium funiculosum*, *Penicillium melinii*, and *Penicillium janthinellum*. Then the first to third mutanase-producing microorganisms are discriminatable from these known mutanase-producing microorganisms.

With respect to the above-mentioned properties, the strains of the first to third mutanase-producing microorganisms are distinct from known strains.

We deposited a first strain, *Bacillus sp.* RM1 which is a novel mutanase-producing microorganism to the National Institute of Bioscience and Human-Technology, Japanese Agency of Industrial Science and Technology as Deposit No. 14836 (FERM P-14836). This RM1 strain has the above-specified microbiological properties. The soil from which this strain was isolated was collected in 1994 at Ninomiya-cho, Naka-gun, Kanagawa Prefecture, Japan.

We deposited a second strain, *Bacillus sp.* RM4 which is a novel mutanase-producing microorganism to the National Institute of Bioscience and Human-Technology, Japanese Agency of Industrial Science and Technology as Deposit No. 14837 (FERM P-14837). This RM4 strain has the above-specified microbiological properties. The soil from which this strain was isolated was collected in 1994 at Kusatsu Onsen, Gunma Prefecture, Japan.

We deposited a third strain, *Bacillus sp.* M7 which is a novel mutanase-producing microorganism to the National institute of Bioscience and Human-Technology, Japanese Agency of Industrial Science and Technology as Deposit No. 14835 (FERM P-14835). This M7 strain has the above-specified microbiological properties. The soil from which this strain was isolated was collected in 1993 at Mitama-Fudo, Niigata Prefecture, Japan.

The above-mentioned RM1 and RM4 strains are isolated from the soil by the following screening method.

A spatula of soil is suspended in 5 ml of sterilized physiological saline. The suspension, 100 μl, is spread on an agar medium with mutan added and cultivated at 45° C. for 3 to 5 days. Those colonies which develop halo are isolated as a mutanase-producing microorganism. The microorganism is cultivated and the resulting enzyme is examined for physicochemical properties. Through this screening process, RM1 and RM4 strains were selected which had excellent plaque removing ability and stability in oral compositions.

Mutanase is produced by inoculating the RM1 or RM4 strain in a natural or synthetic culture medium and cultivating under usual conditions. The preferred medium contains components necessary for microorganisms to grow, for example, such as carbon sources, nitrogen sources and inorganic salts. Nutrients for the medium are those commonly used for microorganisms, for example, glucose, inositol, fructose, mutan, and starch as the carbon source, peptone, soybean powder and yeast extract as the nitrogen source, and salts of phosphoric acid, sodium, potassium and magnesium as the inorganic salt. These nutrients may be used alone or in admixture of two or more. Preferred among others are inositol, mutan, peptone and phosphates. The culture medium should be at pH 5 to 8.5 for the first mutanase-producing microorganism and at pH 5 to 7.5 for the second mutanase-producing microorganism, especially at pH 7 for both of them. The cultivation temperature should be 35° to 48° C., especially 40° C. The cultivation period is generally 1 to 3 days.

The above-mentioned M7 strain is isolated from soil by the following screening method.

A spatula of soil is suspended in 5 ml of sterilized physiological saline solution. The suspension, 100 μl, is spread on an agar medium with mutan added and cultivated at 30° C. for 3 to 5 days. Those colonies which develop halo are isolated as a mutanase-producing microorganism. The microorganism is cultivated and the resulting enzyme is examined for physicochemical properties. Through this screening process, M7 strain was selected which had excellent plaque removing ability and stability in oral compositions.

Mutanase is produced by inoculating the M7 strain in a natural or synthetic culture medium and cultivating under usual conditions.. The preferred medium is contains components necessary for microorganisms to grow, for example, such as carbon sources, nitrogen sources and inorganic salts. Nutrients for the medium are those commonly used for microorganisms, for example, inositol, galactose, and mutan as the carbon source, peptone, polypeptone, soybean powder and yeast extract as the nitrogen source, and salts of phosphoric acid, sodium, potassium and magnesium as the inorganic salt. These nutrients may be used alone or in admixture of two or more. Preferred among others are inositol, mutan, polypeptone and phosphates. The culture medium should be at pH 6 to 8, especially at pH 7. The cultivation temperature is preferably 20° to 33° C., especially 30° C. The cultivation period is generally 1 to 3 days.

Bacterial cells are removed by centrifugation or filtration from the cultivated medium of each strain. The supernatant is recovered as a crude enzyme solution which contains the enzyme of the invention. This crude enzyme solution may be used directly although it is preferable to further purify. The purification methods are, for example, ultrafiltration, vacuum concentration, salting-out using ammonium sulfate, etc., precipitation using ethanol, etc., isoelectric point precipitation, and column chromatography. These methods may be used individually or in combination. This purification is desirably carried out until a single band is confirmed by SDS-polyacrylamide gel electrophoresis.

It is understood that the present invention for the production of mutanase is also applicable to both mutants derived from these strains and recombinant microorganisms carrying the mutanase gene.

In the above-mentioned aspect, the mutanase to be blended according to the invention is one obtained by cultivating the above-mentioned mutanase-producing microorganisms. In another aspect, the mutanase to be blended according to the invention is one having the following physicochemical properties.

(1) action: It is able to cleave $\alpha$-1,3-glucosidic links of mutan.

(2) substrate specificity: It is able to effectively decompose mutan.

(3) optimum pH: It has an optimum pH range of pH 4 to 4.5 when reacting on a mutan substrate at 35° C. for 10 minutes.

(4) stable pH: It is stable in the range of pH 4 to 10 when kept at 25° C. for 24 hours.

(5) optimum temperature: It has an optimum temperature in the range of 50° to 65° C. when reacting on a mutan substrate at pH 5.

(6) thermal stability: Its activity remains stable below 50° C. after incubation at pH 5 for 10 minutes.

(7) effect of metal ions: Mercury and silver show inhibitory effect on a mutan substrate.

(8) effect of inhibitors: p-chloromercurybenzoic acid (PCMB) shows inhibitory effect on a mutan substrate.

(9) molecular weight: It has a molecular weight in the range of about 140,000 to about 160,000 as determined by SDS-polyacrylamide gel electrophoresis.

Mutan used as a substrate in specifying the above-mentioned properties is obtained by well-known methods, for example, by cultivating *Streptococcus mutans* or *Strep-*

*tococcus sobrinus* to produce insoluble glucan and cleaving α-1,6 links of the insoluble glucan with dextranase.

Preferred mutanases are mutanase that the first mutanase-producing microorganism produces (mutanase A having the properties shown below), mutanase that the second mutanase-producing microorganism produces (mutanase B having the properties shown below), and mutanase that the third mutanase-producing microorganism produces (mutanase C having the properties shown below).

Mutanase A (1) action: It is able to cleave α-1,3 links of mutan.

(2) substrate specificity: It is able to effectively decompose mutan.

(3) optimum pH: Its action is optimum at pH 4 when reacting on a mutan substrate at 35° C. for 10 minutes and conserved at pH 4 to 6.

(4) stable pH: It is stable in the range of pH 4 to 10 when kept at 25° C. for 24 hours.

(5) optimum temperature: Its action is optimum at a temperature of 60° C. when reacting on a mutan substrate at pH 5.

(6) thermal stability: Its activity is stable below 60° C. and it is inactivated at 75° C. after incubation at pH 5 for 10 minutes.

(7) effect of metal ions: Mercury, silver and ferric ion show inhibitory effect on a mutan substrate.

(8) effect of inhibitors: PCMB shows inhibitory effect on a mutan substrate.

(9) molecular weight: It has a molecular weight of about 150,000 as determined by SDS-polyacrylamide gel electrophoresis.

Mutanase B (1) action: It is able to cleave α-1,3 links of mutan.

(2) substrate specificity: It is able to effectively decompose mutan.

(3) optimum pH: Its action is optimum at pH 4.5 when reacting on a mutan substrate at 35° C. for 10 minutes and conserved at pH 4 to 7.

(4) stable pH: It is stable in the range of pH 4 to 11 when kept at 25° C. for 24 hours.

(5) optimum temperature: its action is optimum at a temperature of 65° C. when reacting on a mutan substrate at pH 5.

(6) thermal stability: Its activity is stable below 60° C. and it is inactivated at 75° C. after incubation at pH 5 for 10 minutes.

(7) effect of metal ions: Mercury and silver show inhibitory effect on a mutan substrate.

(8) effect of inhibitors: PCMB shows inhibitory effect on a mutan substrate.

(9) molecular weight: It has a molecular weight of about 140,000 as determined by SDS-polyacrylamide gel electrophoresis.

Mutanase C (1) action: It is able to cleave α-1, 3 links of mutan.

(2) substrate specificity: It is able to effectively decompose mutan.

(3) optimum pH: Its action is optimum at pH 4.5 when reacting on a mutan substrate at 35° C. for 10 minutes and conserved at pH 4 to 5.

(4) stable pH: It is stable in the range of pH 4 to 10 when kept at 25° C. for 24 hours.

(5) optimum temperature: Its action is optimum at a temperature of 50° C. when reacted on a mutan substrate at pH 5.

(6) thermal stability: Its activity is stable below 50° C. after incubation at pH 5 for 10 minutes.

(7) effect of metal ions: Mercury and silver show inhibitory effect on a mutan substrate.

(8) effect of inhibitors: PCMB shows inhibitory effect on a mutan substrate.

(9) molecular weight: It has a molecular weight of about 160,000 as determined by SDS-polyacrylamide gel electrophoresis.

The properties of mutanases A to C are described in more detail.

(1) Enzymatic action

Mutanase or α-1,3-glucanase is classified into an exo type of terminal incision and an endo type of random incision. It is presumed that mutanases A to C according to the invention have a property to cleave α-1,3 links in the endo type pattern.

More illustratively, 50 µl of a mutanase solution according to the invention or Novozym 234 (trade name, Novo Nordisk A/S, originating from *Trichoderma hargianum*) capable of decomposing α-1,3 links was added to 100 µl of 3% mutan solution. The mixture was incubated at 37° C. for 20 hours. The reaction product was centrifuged to obtain a supernatant, which was spotted on a thin layer chromatography plate and developed with a mixture of 1- butanol/isopropanol/water=4/7/1. Conc. sulfuric acid was sprayed on the plate, which was heated at 100° C. for 5 minutes. The saccharides could be detected as colored spots. The spots of cleaved products by these mutanases showed lower mobility than that of glucose. In the case of Novozym 234, it showed same mobility with glucose. Based on this observation, mutanases A to C according to the invention are confirmed to be endo type enzymes.

(2) Substrate specificity

Mutanases A to C according to the invention are effective for decomposing mutan.

More illustratively, 100 µl of a solution of mutanase A, B or C according to the invention (500 units/ml) was incubated for 30 minutes with 100 µl of a 1% solution of each substrate shown in Table 3. The amount of reducing sugar was detected by the method described below. The results are also shown in Table 3. The hydrolysis rate reported in Table 3 is a relative value expressed on the assumption that the rate for mutan is 100.

Measurement of Enzymatic Activity

To 100 µl of a 0.1M acetic acid buffer containing 3% mutan (pH 5) was added 100 µl of the mutanase solution. The mixture was incubated at 35° C. for 10 minutes with shaking at 100 strokes/min. Reaction was terminated by adding 0.4 ml of a 4,6-dinitrosalicylic acid (DNS) solution. The reaction mixture was centrifuged and 0.5 ml of the supernatant was transferred into a test tube. The tube was capped with a glass ball and kept in boiling water for 10 minutes. The tube was cooled with water for 5 minutes. Then 4 ml of distilled water was added and optical absorbance measured at 530 nm. A titer was determined using glucose as standard. The amount of enzyme which releases 1 µg of reducing sugar per minute is defined as one unit. It is noted that the enzymatic activity referred to below in conjunction with any of physicochemical properties is measured by this method.

TABLE 3

| Substrate | Linkage | Hydrolysis rate (relative value) |
|---|---|---|
| Mutan | α-1,3 | 100 |
| Nigeran | α-1,3 and α-1,4 | 0 |
| Dextran | α-1,6 | 0 |
| Amylose | α-1,4 | 0 |
| Pullulan | α-1,4 and α-1,6 | 0 |
| Laminariheptaose | α-1,3 | 0 |
| Cellohexaose | α-1,6 | 0 |
| p-nitrophenyl-α-D-glucoside |  | 0 |
| p-nitrophenyl-β-D-glucoside |  | 0 |

(3) Optimum pH

Figure 1:
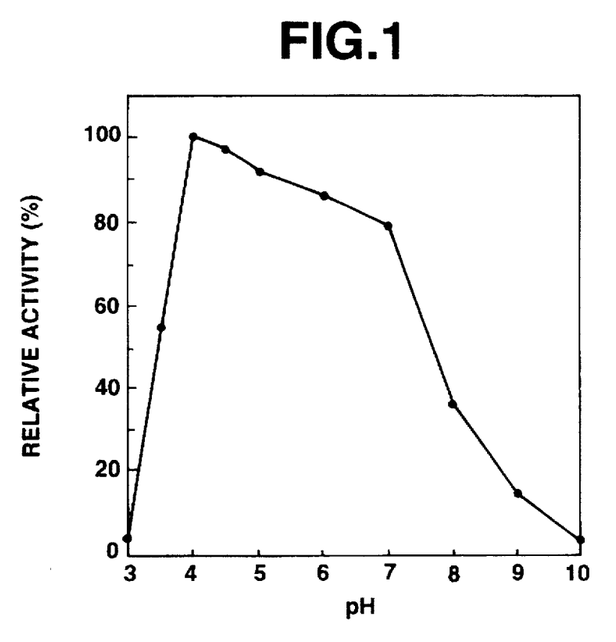
FIGS. 1, 2 and 3 are graphs showing the optimum pH of mutanase A, B and C, respectively.
Figure 2:
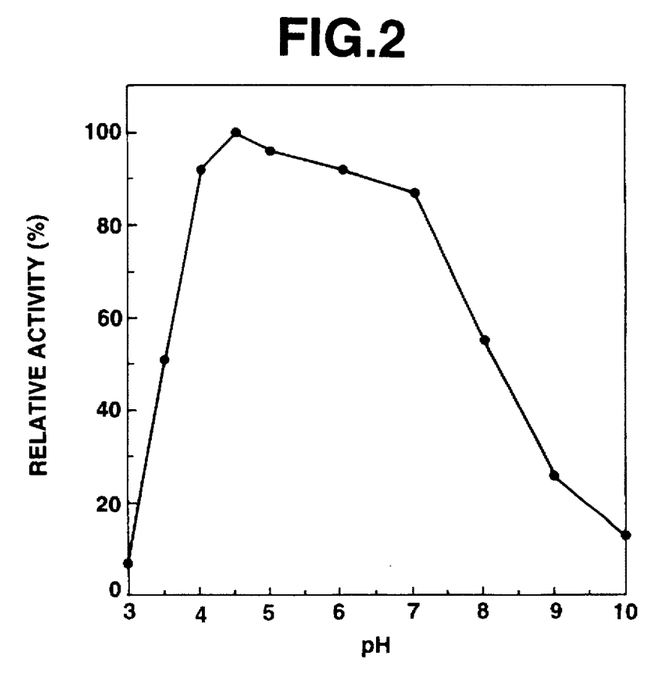
Figure 3:
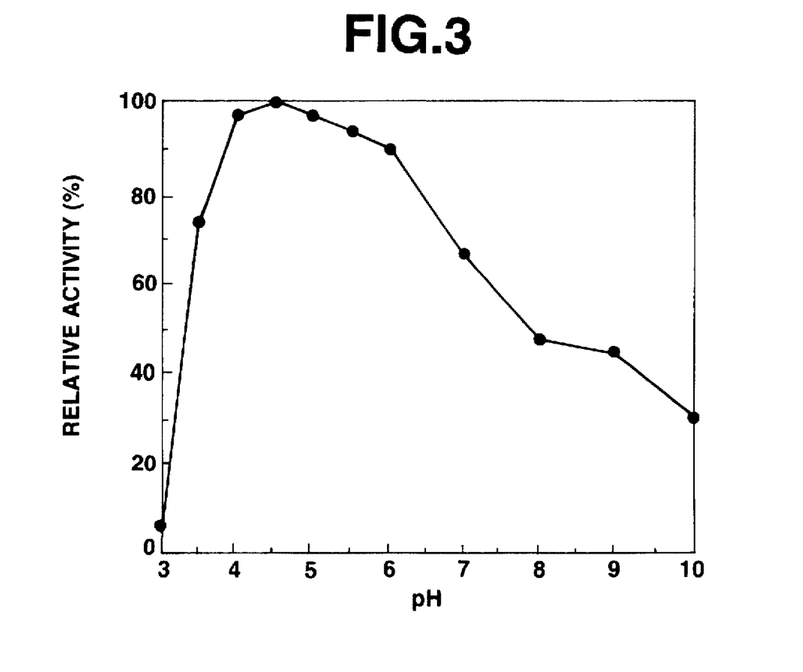

Buffers containing 3% mutan were prepared as follows.
Buffer
pH 3 to 7: citric acid/$Na_2HPO_4$ buffer
pH 3 to 7: $NaH_2PO_4$/$Na_2HPO_4$ buffer
pH 9 to 10: glycine/NaOH buffer
pH 10 to 11: $Na_2HPO_4$/NaOH buffer Mutanase according to the invention was added to the buffer in an amount of 50 units/ml. The reaction mixture was incubated at 35° C. for 10 minutes. The relative activity at a certain pH value is expressed based on the assumption that the activity at optimum pH is 100%. The pH profiles of mutanases A, B and C according to the invention are shown in FIGS. 1 to 3. The action of mutanase A is optimum at pH 4 and conserved at pH 4 to 6 as shown in FIG. 1. The action of mutanase B is optimum at pH 4.5 and conserved at pH 4 to 7 as shown in FIG.2. The action of mutanase C is optimum at pH 4.5 and conserved at pH 4 to 5 as shown in FIG. 3.

(4) Stable pH range

Figure 4:
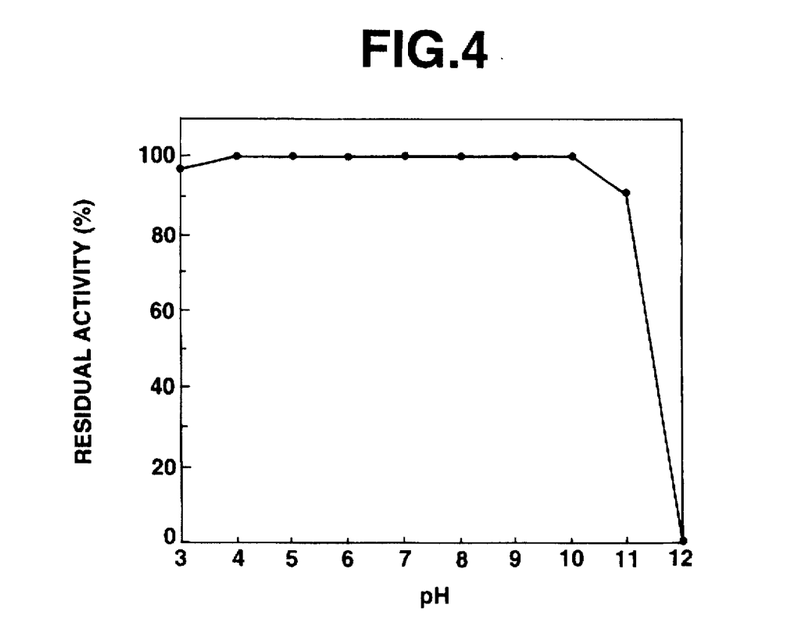
FIGS. 4, 5 and 6 are graphs showing the pH stability of mutanase A, B and C, respectively.
Figure 5:
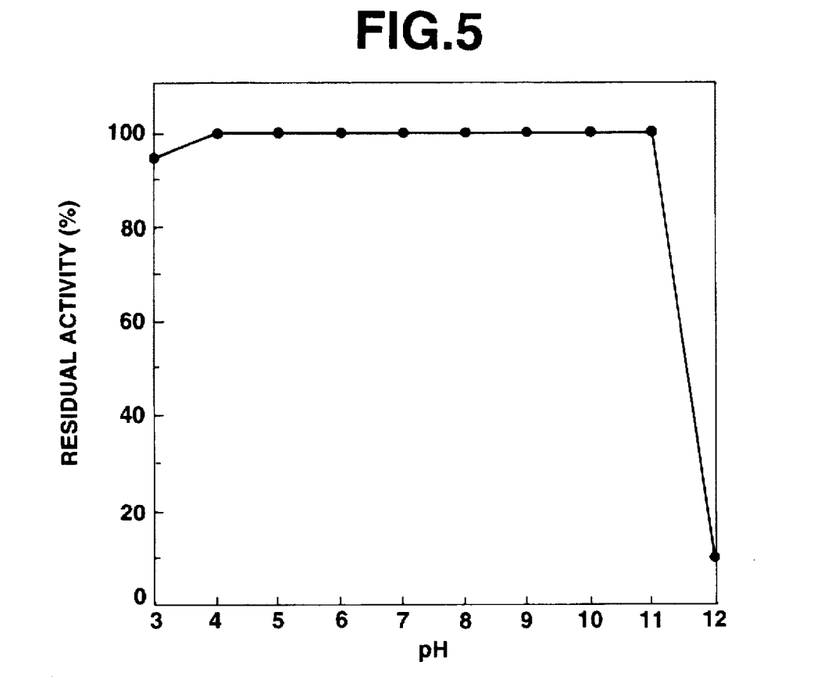
Figure 6:
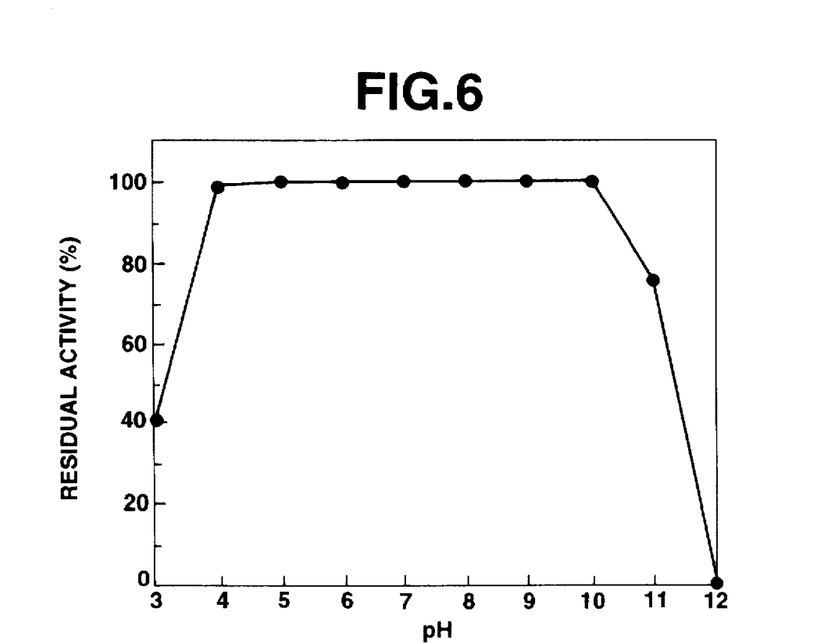

Mutanase according to the invention was added to the above-mentioned 20 mM buffer in an amount of 300 units/ml. After incubation at 25° C. for 24 hours, residual activity was measured. The percent residual activity at a certain pH value is expressed based on the assumption that the initial activity is 100%. For mutanases A, B and C according to the invention, the residual activities at various pH values are shown in FIGS. 4 to 6. Mutanase A showed a residual activity of nearly 100% in the range of pH 4 to 10 and a residual activity of more than 90% even at pH 3 or pH 11 as shown in FIG. 4. Mutanase B showed a residual activity of nearly 100% in the range of pH 3 to 11 as shown in FIG. 5. Mutanase C showed a residual activity of nearly 100% in the range of pH 4 to 10, a residual activity of more than 70% at pH 11, and a residual activity of more than 40% at pH 3 as shown in FIG. 6.

(5) Optimum temperature

Figure 7:
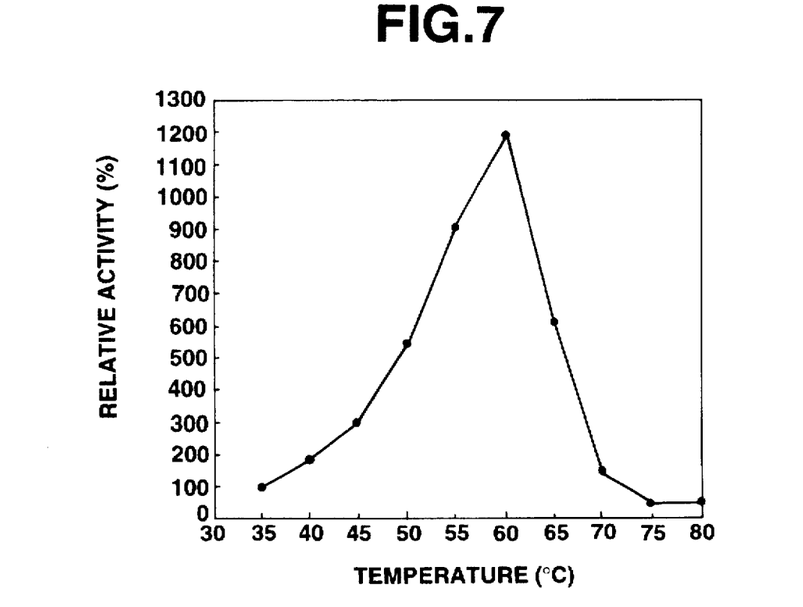
FIGS. 7, 8 and 9 are graphs showing the optimum temperature of mutanase A, B and C, respectively.
Figure 8:
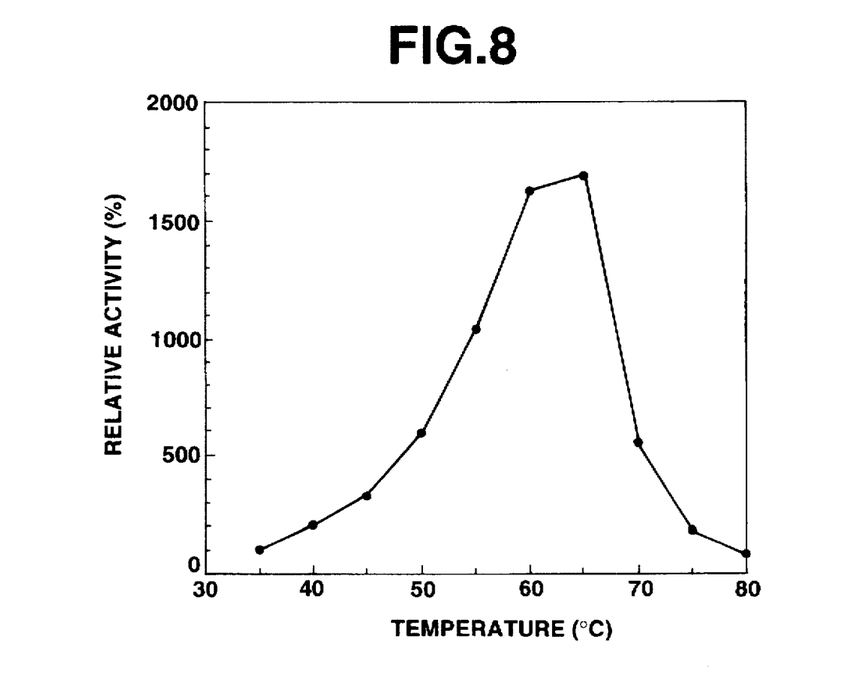
Figure 9:
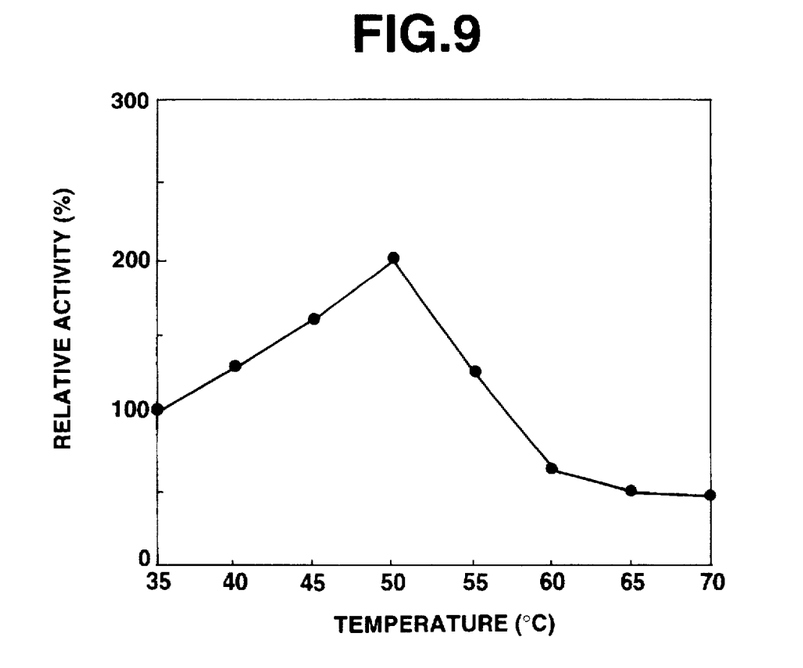

To a 20 mM acetic acid buffer at pH 5 containing 3% of mutan, mutanase according to the invention was added in an amount of 50 units/ml. Reaction was carried out at various temperatures for 10 minutes. The relative activity at a certain temperature is expressed based on the assumption that the activity at 35° C. is 100%. For mutanases A, B and C according to the invention, the relative activities at various temperatures are shown in FIGS. 7 to 9. Mutanase A showed optimum action at 60° C. as shown in FIG. 7. Mutanase B showed optimum action at 65° C. as shown in FIG. 8. Mutanase C showed optimum action at 50° C. as shown in FIG. 9.

(6) Thermal stability

Figure 10:
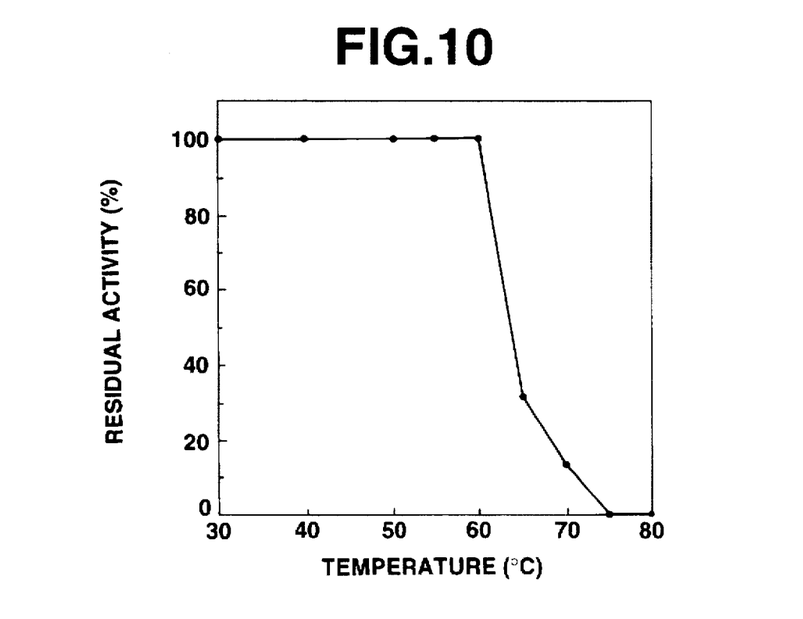
FIGS. 10, 11 and 12 are graphs showing the thermal stability of mutanase A, B and C, respectively.
Figure 11:
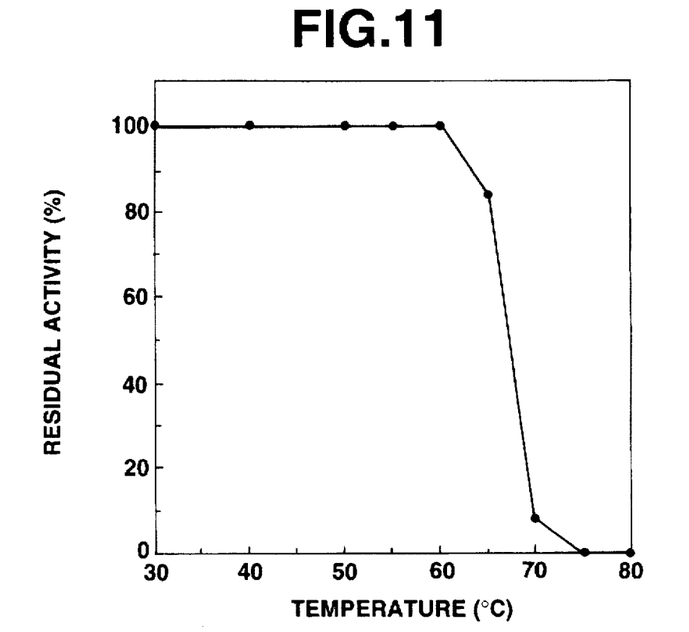
Figure 12:
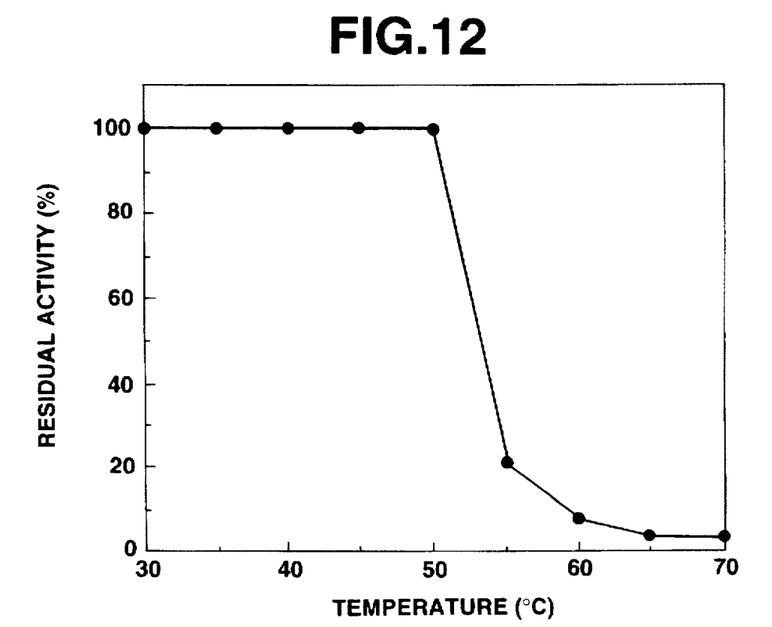

With 20 mM acetic acid buffer (pH 5) was prepared 300 units/ml of mutanase solution according to the invention. The enzyme solution was incubated at various temperatures for 10 minutes and ice cooled. The percent residual activity is expressed based on the assumption that the enzymatic activity of an untreated sample is 100%. For mutanases A, B and C according to the invention, the residual activities at various temperatures are shown in FIGS. 10 to 12. Mutanase A had a residual activity of 100% at 30° to 60° C. and 30% at 65° C. and was denatured at 75° C., as shown in FIG. 10. Mutanase B had a residual activity of 100% at 30° to 60° C. and about 85% at 65° C. and was denatured at 75° C., as shown in FIG. 11. Mutanase C had a residual activity of 100% at 30° to 50° C. and 22% at 55° C., as shown in FIG. 12.

(7) Effect of metal ions

Mutanase according to the invention was added to a 50 mM acetic acid buffer (pH 5) in an amount of 50 units/ml. Various metal salts were individually added thereto in a final concentration of 1 mM. The solution was incubated at 35° C. for 30 minutes. The relative activity is expressed based on the assumption that the enzymatic activity of a metal salt-free sample is 100%. For mutanases A, B and C according to the invention, the relative activities were determined in this way and shown in Table 4. As seen from Table 4, mutanase A is inhibited by the addition of mercury, silver and ferric ion; and mutanases B and C are inhibited by mercury and silver.

TABLE 4

| | Relative activity (%) Mutanase | | |
|---|---|---|---|
| Metal ion | A | B | C |
| none | 100 | 100 | 100 |
| $Ca^{2+}$ | 98 | 97 | 98 |
| $Cu^{2+}$ | 98 | 100 | 100 |
| $Fe^{2+}$ | 100 | 100 | 96 |
| $Fe^{3+}$ | 61 | 96 | 99 |
| $Zn^{2+}$ | 100 | 95 | 91 |
| $Ag^{2+}$ | 67 | 60 | 56 |
| $Hg^{2+}$ | 6 | 13 | 27 |

(8) Effect of inhibitors

Mutanase according to the invention was added to a 50 mM acetic acid buffer (pH 5) in an amount of 50 units/ml. Various inhibitors were individually added thereto in a final concentration of 1 mM. The solution was incubated at 35° C. for 30 minutes. The relative activity is expressed based on the assumption that the enzymatic activity of an inhibitor-free sample is 100%. For mutanases A, B and C according to the invention, the relative activities were determined in this way and shown in Table 5. As seen from Table 5, the addition of p-chloromercury benzoate (PCMB) strongly inhibits mutanases A, B and C.

TABLE 5

| | Relative activity (%) Mutanase | | |
|---|---|---|---|
| Inhibitor | A | B | C |
| none | 100 | 100 | 100 |
| Iodoacetic acid | 100 | 99 | 87 |
| N-ethylmaleimide | 100 | 98 | 94 |
| PCMB | 6 | 14 | 11 |
| 2Na-EDTA | 93 | 99 | 79 |

(9) Molecular weight

Using 5 to 20% polyacrylamide gradient gel (Ready Made Gel by Biorad K.K.), purified mutanase according to the invention was subject to electrophoresis at 40 mA for one hour. Molecular weight was determined using Sigma Marker (trade name, Sigma Chemical Co.). Mutanase A had a molecular weight of about 150,000, mutanase B had a molecular weight of about 140,000, and mutanase C had a molecular weight of about 160,000.

Insofar as it has the above-mentioned physicochemical properties, the mutanase according to the invention is not limited by its original enzyme. Although mutanases produced from RM1, RM4 and M7 strains generally suffice, mutanases produced from RM1, RM4 and M7 strains can be converted into more stable and more effective enzymes by chemical modification or protein engineering.

The mutanases according to the invention have the above-mentioned physicochemical properties and are distinguishable from well-known mutanases in many points. For example, mutanases A to C according to the invention and Novozym 234 are distinct in the pattern of cleaving $\alpha$-1,3 links. Mutanase A has an optimum pH value of 4 and an optimum temperature of 60° C., mutanase B has an optimum temperature of 65° C., and mutanase C has a stable pH range of pH 4 to 10 (25° C., 24 hours) and a molecular weight of about 160,000 whereas the mutanase originating from BC-8 strain has an optimum pH value of 4.5, an optimum temperature of 45° to 50° C., a stable pH range of pH 7.0 to 9.0, and a molecular weight of about 180,000. Mutanase A has a molecular weight of about 150,000, an optimum temperature of 60° C. and an optimum pH value of 4, mutanase B has a molecular weight of about 140,000, an optimum temperature of 65° C. and an optimum pH value of 4.5, mutanase C has a molecular weight of about 160,000, an optimum temperature of 50° C. and an optimum pH value of 4.5 whereas the mutanase originating from FERM-P4765 strain has a molecular weight of more than about 70,000, an optimum temperature of 30° to 40° C. and an optimum pH value of 6.2 to 6.7. The mutanases described in JP-A 34980/1977, 145583/1975 and 9743/1972 are produced by microorganisms belonging to the genus Streptomyces, microorganisms belonging to the genus Flavobacterium, and microorganisms of *Trichoderma hargianum, Penicillium lilacinum, Penicillium funiculosum, Penicillium melinii,* and *Penicillium janthinellum,* respectively. For example, the mutanase described in JP-A 34980/1977 has an optimum pH value of 5.5 and a stable pH range of 5 to 7, the mutanase described in 145583/1975 has an optimum pH value of 6.0 and a stable pH range of 5.0 to 7.0. They are different in many physicochemical properties from the mutanases of the invention. It is noted that the physicochemical properties of the mutanase described in 9743/1972 are unknown.

In the oral composition of the invention, the mutanase is preferably blended in an amount of 1 to 50,000 units/gram, more preferably 10 to 10,000 units/gram. Less than 1 unit/gram of mutanase would be ineffective for preventing dental caries whereas more than 50,000 units/gram of mutanase would adversely affect the sensitivity to the mouth of the oral composition.

One unit of mutanase is the amount of enzyme which releases an amount of free reducing sugar corresponding to 1 µg of glucose per minute on mutan substrate. The mutan used herein is water insoluble white powder obtained when dextranase acts on the insoluble glucan ($\alpha$-1,3 and $\alpha$-1,6 -bonds) produced by *Streptococcus mutans* strain 6715 (see Carbohydrate Research, vol. 38, 1974).

In the practice of the invention, the mutanase may be used alone or in admixture with other enzymes, for example, dextranase, amylase, lysozyme, protease, and lytic enzymes. Particularly when used in combination with dextranase, mutanase becomes more effective for inhibiting dental plaque formation.

The dextranase used herein may be any of well-known ones, for example, one originating from *Chaetomium sp.* Dextranase is preferably blended in an amount of 10 to 50,000 units/gram, more preferably 200 to 20,000 units/gram of the oral composition. Less than 10 unit/gram of dextranase would be ineffective for restraining dental plaque formation whereas more than 50,000 units/gram of dextranase would adversely affect the feel to the mouth of the oral composition.

One unit of dextranase is the amount of enzymes which releases an amount of free reducing sugar corresponding to 1 µg of glucose per minute on reaction with dextran as a substrate.

In the oral composition of the invention, well-known ingredients may be blended in accordance with a particular application or form of composition.

In the case of dentifrice, for example, there may be blended other ingredients including abrasives, binders, humectants, surfactants, sweeteners, preservatives and coloring agents.

Examples of the abrasive include aluminum oxide, aluminum hydroxide, dibasic calcium phosphate dihydrate and anhydride, silica abrasives, calcium carbonate, calcium pyrophosphate, aluminum silicate, insoluble sodium metaphosphate, tribasic magnesium phosphate, calcium sulfate, and synthetic resins alone or in admixture. The abrasive is generally blended in an amount of about 10 to 90% by weight of the entire composition, typically 10 to 60% by weight of the toothpaste. In the present invention, it is preferred to use silica abrasive as a main abrasive because the effectiveness of mutanase is further enhanced. Examples of the silica abrasive include precipitated silica, silica gel, aluminosilicate, and zirconosilicate. Abrasives having a particle size of about 1 to 30 µm are preferred from the standpoint of sensitivity on use of dentifrice.

Examples of the binder include carrageenan, sodium carboxymethyl cellulose, alkali metal salts of alginic acid such as sodium alginate, gums, polyvinyl alcohol, and beegum. The binder is generally blended in an amount of about 0.3 to 5% by weight of the entire composition. Examples of the humectant include sorbitol, glycerin, propylene glycol, 1,3-butylene glycol, polyethylene glycol, xylytol, maltitol, and lactitol. The humectant is generally blended in an amount of about 10 to 70% by weight of the entire composition.

Examples of the surfactant include anionic surfactants such as sodium laurylsulfate, lauroyl sarcosinate, $\alpha$-olefin sulfonates, thaurates, lauryl monoglyceride sulfate, and soap; nonionic surfactants such as lauric acid diethanol amide, stearyl monoglyceride, sucrose fatty acid esters, lactose fatty acid esters, lactitol fatty acid esters, maltitol fatty acid esters, polyoxyethylene sorbitan monostearate; and ampholytic surfactants including betain and amino acid types. The surfactant is generally blended in an amount of about 0.5 to 7% by weight of the entire composition.

Examples of the sweetener include sodium saccharin, stevioside, neohesperidyl dihydrochalcone, thaumatine, glycyrrhizin, and perillartine. Flavors include anethole, carvone, cineole, methyl salicylate, eugenol, ethyl butyrate, and cinnamic aldehyde, and essential oils containing these flavor components such as spearmint oil, peppermint oil and wintergreen oil. Exemplary preservatives are p-hydroxybenzoates and sodium benzoate.

A dentifrice composition, typically toothpaste according to the invention can be prepared by kneading the above-mentioned components with a suitable amount of water. The resulting toothpaste is contained in a suitable container, for example, tubular containers such as aluminum tubes, laminate tubes made of aluminum foil having plastic film laminated on each surface, and plastic tubes, bottles, and aerosol containers.

When the oral composition of the invention is a mouthwash, for example, there may be blended other ingredients including humectants, sweeteners, pH adjusting agents, preservatives and solvents. Examples of the pH adjusting agent include organic acids such as citric acid, phosphoric acid, malic acid, and acetic acid. The solvents include ethanol and water. Any other suitable components may be blended if desired.

In the case of chewing gum and troche, conventional ingredients used therein may be blended in conventional amounts and a conventional technique may be used for preparation.

In the oral composition of the invention, enzymes other than mutanase and dextranase may be blended as well as fluorine compounds such as sodium fluoride and sodium monofluorophosphate, antibodies, stannous compounds, chlorhexidine salts, epsilon-aminocaproic acid, tranexamic acid, aluminum chlorhexidyl allantoin, dihydrocholesterol, glycyrrhetinic acid and salts, sodium chloride, and water-soluble inorganic phosphoric acids. Examples of the water-soluble inorganic phosphoric acid which can be blended in the oral composition of the invention include potassium and sodium salts of orthophosphoric acid, pyrophosphoric acid, and polyphosphoric acid.

EXAMPLE

Examples of the present invention are given below by way of illustration and not by way of limitation. Experiments are first described.

Preparation Example (1) Preparation of mutan

Mutan used in the following examples was prepared as follows.

*Streptococcus sobrinus* strain 6715 was inoculated in 200 ml of BHI medium (Brain Heart Infusion by Oxoid Company) and cultivated at 37° C. for one day. The resulting culture was inoculated in 4 liters of BHI medium containing 5% sucrose and cultivated at 37° C. for 5 days. The precipitate was harvested, dissolved in 500 ml of 1N sodium hydroxide solution, and allowed to stand at room temperature for one hour. After centrifugal separation, the supernatant was neutralized with hydrochloric acid. The precipitate was recovered by filtration. Dextranase was added to the recovered precipitate for cleaving α-1,6 links.

(2) Preparation of mutanase

Mutanase used in the following examples was prepared as follows.

First of all, a culture medium of the following composition was prepared.

| Medium composition | |
|---|---|
| Inositol | 10 g/l |
| Mutan | 1 g/l |
| Peptone | 5 g/l |
| Yeast extract | 3 g/l |
| $KH_2PO_4$ | 2 g/l |
| $NH_4NO_3$ | 2 g/l |
| $MgSO_4.7H_2O$ | 0.3 g/l |
| pH 7.0 | |

Mutanase A

The RM1 strain obtained by the above-mentioned screening method was inoculated in the above medium and cultivated at 40° C. for 2 days. The medium was centrifuged at 8,000 rpm for 15 minutes to collect a supernatant, which was concentrated by ultrafiltration. An amount of ammonium sulfate was added to the supernatant to provide 90% saturation. The mixture was thoroughly stirred, kept in ice for more than one hour, and then centrifuged. The precipitate was recovered. It was suspended in 10 mM Tris-hydrochloric acid buffer (pH 8) and dialyzed against the same buffer. The dialyzed sample was centrifuged at 8,000 rpm for 10 minutes. The resulting supernatant contained the mutanase of the present invention (designated RM1 enzyme). It was purified as follows. It was applied to an anion exchange chromatograph DE52 (trade name: Whatman Co.) (pH 8.0) and unabsorbed fractions were collected. These fractions were dialyzed against 10 mM Tris-HCl buffer (pH 8.5) and then applied to DE52 (pH 8.5). Mutanase was eluted with a linear gradient concentration of NaCl from 0 to 0.2M, yielding the purified enzyme.

Mutanase B

The RM4 strain obtained by the above-mentioned screening method was inoculated in the above medium and cultivated at 40° C. for 2 days. The medium was centrifuged at 8,000 rpm for 15 minutes to collect a supernatant, which was concentrated by ultrafiltration. An amount of ammonium sulfate was added to the supernatant to 90% saturation. The mixture was thoroughly stirred, kept in ice for more than one hour, and then centrifuged. The precipitate was recovered. It was suspended in 10 mM Tris-hydrochloric acid buffer (pH 8) and dialyzed against the same buffer. The dialyzed sample was centrifuged at 8,000 rpm for 10 minutes. The resulting supernatant contained the mutanase of the present invention (designated RM4 enzyme). It was purified as follows. It was applied to an anion exchange chromatograph DEAE-Toyopearl 650M (trade name: Toso K.K.) (pH 7.0) and unabsorbed fractions were collected. Unabsorbed fractions were similarly collected through DEAE-Toyopearl 650 (pH 8.5). Mutanase active fractions were then collected by means of a gel permeation chromatograph Sephacryl S-300HR (trade name, Pharmacia), obtaining a purified enzyme.

Mutanase C

The M7 strain obtained by the above-mentioned screening method was inoculated in the above medium and cultivated at 30° C. for 2 days. The medium was centrifuged at 8,000 rpm for 15 minutes to collect a supernatant, which was concentrated by means of a ultrafiltration apparatus (Amicon Co.). An amount of ammonium sulfate was added to the supernatant to 90% saturation. After salting out, the precipitate was suspended in 10 mM Tris-hydrochloric acid buffer (pH 8), which was dialyzed overnight. The dialyzed solution was applied to an anion exchange chromatograph DE52 (trade name: Whatman Co.) equilibrated with 10 mM Tris-hydrochloric acid buffer (pH 8). An eluate containing the mutanase of the invention (designated M7 enzyme) was obtained as unabsorbed fractions. The eluate was dialyzed against 10 mM acetic acid buffer (pH 4.8). The dialyzed eluate was applied to a cation exchange chromatograph CM-Toyopearl 650M (Toso K.K.) equilibrated with 10 mM acetic acid buffer (pH 4.8) whereby M7 enzyme was adsorbed. The adsorbed M7 enzyme was eluted with 10 mM acetic acid buffer (pH 4.8) containing 0 to 0.2M sodium chloride solution in a linear gradient manner.

A mixture of the M7 enzyme solution and the same volume of 0.1M phosphate buffer containing 1M ammonium sulfate (pH 7.0) was applied to a hydrophobic chromatograph equilibrated with 50 mM phosphate buffer (pH 7.0) containing 0.5M ammonium sulfate. The M7 enzyme was eluted by reducing the ammonium sulfate concentration from 0.5M to 0M. The resulting active fraction was dialyzed against 10 mM phosphate buffer (pH 7.0). M7 enzyme was purified in this way.

The purified RM1, RM4 and M7 enzymes were examined for physicochemical properties, finding-that they had the above-mentioned physicochemical properties the mutanase according to the invention should have. The results of examination for physicochemical properties on the purified RM1, RM4 and M7 enzymes are as previously described and shown in FIGS. 1 to 12 and Tables 1 to 5.

Experiment 1
Evaluation of effectiveness to remove plaque

Streptococcus mutans strain 10449 was incubated in a static culture using brain heart infusion (BHI) broth at 37° C. overnight to form a pre-culture medium. This pre-culture medium, 100 μl, was added to 3 ml of BHI containing 1% sucrose in a M2 test tube. With the test tube set slant, static culture was carried out at 37° C. overnight to form plaque on the tube wall. With the medium discarded, the tube interior was washed twice with distilled water. Then 3 ml of artificial saliva solution (0.85 mM $CaCl_2$, 6.22 mM $KH_2PO_4$, 50 mM NaCl, 0.15 mM $MgCl_2$, pH 5.94) was added, and 1 ml of each of the enzymes shown in Table 6 was added to the test tube, which was kept at 37° C. for 3 minutes. Thereafter, the enzyme solution was discarded, and the tube interior was washed twice with distilled water. Distilled water, 4 ml, was then added to the tube which was subject to ultrasonic treatment. The solution was measured for turbidity. Using an enzyme-free sample as a control, the plaque removal capability of each enzyme solution was calculated. It is noted that on examination of dextranase copresent systems, an enzyme solution containing 10 units of RM1, RM4 or M7 enzyme or Novozym 234 and 2,000 units of dextranase was used after addition of artificial saliva solution. The results are shown in Table 6.

TABLE 6

| Enzyme sample | | Plaque removal (%) |
|---|---|---|
| Dextranase | 2000 units | 15 |
| Novozym 234 | 10 units | 0 |
| Novozym 234 | 500 units | 9 |
| RM1 enzyme | 10 units | 0 |
| RM4 enzyme | 10 units | 0 |
| M7 enzyme | 10 units | 0 |
| M7 enzyme | 500 units | 90 |
| Dextranase + Novozym 234 | 2000 units 10 units | 50 |
| Dextranase + RM1 enzyme | 2000 units 10 units | 70 |
| Dextranase + RM4 enzyme | 2000 units 10 units | 70 |

As seen from Table 6, mutanase combined with dextranase exerts a synergistic effect in removing plaque. That effect is greater with the inventive enzymes than with Novozym 234. It is thus believed that a mutanase of the endo type is superior as a plaque removing enzyme. With respect to the plaque that Streptococcus mutans strain 10449 forms, M7 enzyme exhibits outstanding plaque removal capability.

Experiment 2
Animal test

An animal test was done for examining the caries preventive effect of the three mutanases: RM1, RM4 and M7 enzymes.

The caries model used herein included several groups each consisting of ten 3-week old male golden hamsters. The hamsters were infected with a streptomycin-resistant caries causing bacterium, Streptococcus mutans strain 10449. Infection was carried out by inoculating one platinum loop of the strain in 4 ml of BHI medium (manufactured by BBL), incubating under anaerobic conditions at 36° C. for 20 hours, and supplying 0.1 ml of the culture liquid dropwise into the mouth of each hamster. The procedure was repeated 3 days. Fixation of the bacterium in the hamster was confirmed using MS agar plate (manufactured by Difco) containing 0.1% streptomycin. After fixation of the bacterium was confirmed, each of the pharmaceutical agents shown in Table 7 was administered to the hamsters over 5 weeks. The method of administering the pharmaceutical agent was by administering dropwise the agent into the mouth and left and right cheek pouches of a hamster, 0.1 ml each and 0.3 ml in total. This method was repeated twice a day. For the control group, filtered ion-exchanged water was administered dropwise by the same method.

The feed fed during the experimental term was a caries-inducing powder feed Diet 2000 (manufactured by Nihon Crea K.K.). Also fed was ion-exchanged water filtered through a membrane filter with a pore size of 0.2 μm.

A hamster was examined for caries according to Kyese method (J. Dent. Res., Vol. 23, 1944). A caries suppressive rate was calculated according to the following expression.

Caries suppressive rate (%)=|1–(caries score of the pharmaceutical agent administered group)/(caries score of the control group)|×100

The caries suppressive rates of the respective pharmaceutical agents are reported in Table 7.

TABLE 7

| Expt. No. | Sample Type | Amount (U/ml) | Caries suppressive rate (%) |
|---|---|---|---|
| 1 | Control (deionized water) | — | 0 |
| 2 | RM1 enzyme | 400 | 25 |
| 3 | RM1 enzyme + Dextranase | 100 1000 | 54 |
| 4 | RM4 enzyme | 400 | 22 |
| 5 | RM4 enzyme + Dextranase | 100 1000 | 50 |
| 6 | M7 enzyme | 400 | 41 |
| 7 | M7 enzyme + Dextranase | 100 1000 | 62 |

Experiment 3
Stability in preparation

To 10 grams of commercially available toothpaste was added 200 units of RM1 enzyme, RM4 enzyme or Novozym 234. The toothpaste was milled for 10 minutes. The toothpaste was stored at 37° C. for about one month while a sample of 0.8 gram was taken at intervals The sample was suspended in 2.4 ml of phosphate buffer at pH 8, which was centrifuged. The supernatant was measured for enzymatic activity by the same procedure as previously mentioned. The results of residual activity measurement are shown in Table 8.

TABLE 8

| | Residual activity (%) after storage for | | | | |
|---|---|---|---|---|---|
| | 0 | 1 | 3 | 9 | 28 days |
| RM1 enzyme | 100 | 100 | 100 | 100 | 100 |
| RM4 enzyme | 100 | 100 | 100 | 100 | 100 |
| Novozym 234 | 100 | 56 | 39 | 9 | 0 |

It is noted that RM1 and RM4 enzymes were fully stable in preparations such as tooth powder, liquid dentifrice, mouthwash, denture cleaner, gargling tablet, gingival massage cream, troche, and oral paste when 200 units of the enzyme alone or in combination with dextranase was blended per 10 grams of each preparation. Also M7 enzyme was fully stable in preparations such as tooth powder, liquid dentifrice, mouthwash, denture cleaner, gargling tablet, gingival massage cream, troche, and oral paste when 500 units of the enzyme alone or in combination with dextranase was blended per gram of each preparation.

In the following examples, all percents are by weight. The contents of dextranase and mutanase are expressed in unit per gram of the composition.

Example 1: Toothpaste

| | |
|---|---|
| Silica | 20% |
| Sorbitol | 60 |
| Sodium lauryl sulfate | 0.9 |
| Sodium saccharin | 0.15 |
| Gelatin | 0.3 |
| Palmitic acid diethanol amide | 1.5 |
| Propylene glycol | 5 |
| Flavor | 0.3 |
| Anethole | 0.2 |
| l-menthol | 0.7 |
| Sodium lauroyl sarcosinate | 0.5 |
| Sodium fluoride | 0.2 |
| Xanthane gum | 0.5 |
| Polyethylene glycol #4000 | 0.5 |
| Chrorhexidine gluconate | 0.03 |
| Dextranase | 3000 U/g |
| RM1 enzyme | 300 U/g |
| Water | balance |
| Total | 100.0% |

Example 2: Toothpaste

| | |
|---|---|
| Aluminum hydroxide | 45% |
| Sorbitol | 30 |
| Sodium lauryl sulfate | 0.8 |
| Sodium alginate | 0.6 |
| Sodium saccharin | 0.1 |
| Gelatin | 0.2 |
| Lauric acid diethanol amide | 1.6 |
| Propylene glycol | 5 |
| Flavor | 0.3 |
| Anethole | 0.3 |
| l-menthol | 1.0 |
| Sodium lauroyl sarcosinate | 0.4 |
| Sodium fluoride | 0.75 |
| M7 enzyme | 500 U/g |
| Water | balance |
| Total | 100.0% |

Example 3: Toothpaste

| | |
|---|---|
| Aluminum hydroxide | 45% |
| Sorbitol | 30 |
| Sodium lauryl sulfate | 0.8 |
| Sodium alginate | 0.6 |
| Sodium saccharin | 0.1 |
| Gelatin | 0.2 |
| Palmitic acid diethanol amide | 1.6 |
| Propylene glycol | 5 |
| Flavor | 0.3 |
| Carvone | 0.2 |
| l-menthol | 0.7 |
| Sodium lauroyl sarcosinate | 0.4 |
| Sodium fluoride | 0.75 |
| RM1 enzyme | 2000 u/g |
| Water | balance |
| Total | 100.0% |

Example 4: Toothpaste

| | |
|---|---|
| Calcium carbonate | 45% |
| Sorbitol | 24 |
| Sodium lauryl sulfate | 1.3 |
| Carrageenan | 0.7 |
| Sodium alginate | 0.3 |
| Sodium saccharin | 0.1 |
| Gelatin | 0.2 |
| Palmitic acid diethanol amide | 0.8 |
| Propylene glycol | 4 |
| Flavor | 0.7 |
| Eugenol | 0.1 |
| l-menthol | 0.4 |
| Sodium lauroyl sarcosinate | 0.4 |
| Sodium fluoride | 0.75 |
| Dextranase | 2000 U/g |
| RM1 enzyme | 300 U/g |
| Water | balance |
| Total | 100.0% |

Example 5: Toothpaste

| | |
|---|---|
| Dibacic calcium phosphate dihydrate | 50% |
| Sodium lauryl sulfate | 1 |
| Carrageenan | 0.6 |
| Xanthane gum | 0.3 |
| Sodium saccharin | 0.1 |
| Gelatin | 0.2 |
| Palmitic acid diethanol amide | 1 |
| Propylene glycol | 4 |
| Flavor | 0.8 |
| Anethole | 0.1 |
| l-menthol | 0.3 |
| Sodium lauroyl sarcosinate | 0.4 |
| Sodium monofluorophosphate | 0.5 |
| Glycerin | 20 |
| Tranexamic acid | 0.05 |
| Dextranase | 3000 U/g |
| RM1 enzyme | 200 U/g |
| Water | balance |
| Total | 100.0% |

Example 6: Toothpaste

| | |
|---|---|
| Denatured aluminum hydroxide | 50% |
| Sodium lauryl sulfate | 1.5 |
| Carrageenan | 0.5 |

21
-continued

| | |
|---|---|
| Xanthane gum | 0.5 |
| Sodium saccharin | 0.14 |
| Propylene glycol | 5 |
| Flavor | 1.0 |
| Anethole | 0.1 |
| l-menthol | 0.3 |
| Sodium myristoyl sarcosinate | 0.3 |
| Sodium fluoride | 0.5 |
| Glycerin | 20 |
| Silicic anhydride | 5 |
| Titanium oxide | 0.5 |
| Sodium carboxymethyl cellulose | 0.1 |
| Triclosan | 0.04 |
| Dextranase | 5000 U/g |
| RM4 enzyme | 300 U/g |
| Water | balance |
| Total | 100.0% |

Example 7: Liquid dentifrice

| | |
|---|---|
| Silica | 18% |
| Sorbitol | 50 |
| Sodium lauryl sulfate | 1 |
| Sodium saccharin | 0.1 |
| Gelatin | 0.2 |
| Lauric acid diethanol amide | 1.2 |
| Propylene glycol | 2 |
| Flavor | 1.0 |
| Carvone | 0.1 |
| l-menthol | 0.4 |
| Sodium palmitoyl sarcosinate | 0.4 |
| Sodium fluoride | 0.2 |
| Glycerin | 18 |
| Xanthane gum | 0.1 |
| Decaglyceryl laurate | 0.5 |
| Sodium sulfate anhydride | 0.3 |
| Dextranase | 3000 U/g |
| RM1 enzyme | 300 U/g |
| Water | balance |
| Total | 100.0% |

Example 8: Mouthwash

| | |
|---|---|
| Modified ethanol | 1.6% |
| Polyoxyethylene-hardened castor oil | 2 |
| Citric acid | 0.01 |
| Trisodium citrate | 0.3 |
| Flavor | 0.15 |
| Anethole | 0.05 |
| l-menthol | 0.2 |
| Sodium lauroyl sarcosinate | 0.1 |
| Sodium fluoride | 0.08 |
| Glycerin | 10 |
| DL-alanine | 1 |
| Dextranase | 4600 U/g |
| RM1 enzyme | 500 U/g |
| Water | balance |
| Total | 100.0% |

Example 9: Mouthwash

| | |
|---|---|
| 90% ethanol | 20% |
| Polyoxyethylene (80 mol) sorbitan monothaurate | 0.5 |
| Flavor | 1.5 |
| Anethole | 0.3 |

22
-continued

| | |
|---|---|
| l-menthol | 0.8 |
| Sodium monofluorophosphate | 0.15 |
| Sodium lauroyl sarcosinate | 0.1 |
| Dextranase | 2000 U/ml |
| RM1 enzyme | 500 U/ml |
| Water | balance |
| Total | 100.0% |

Example 10: Mouthwash

| | |
|---|---|
| 90% ethanol | 20% |
| Polyoxyethylene (80 mol) sorbitan monothaurate | 0.5 |
| Flavor | 1.5 |
| Anethole | 0.3 |
| l-menthol | 0.8 |
| Sodium monofluorophosphate | 0.15 |
| Sodium lauroyl sarcosinate | 0.1 |
| Dextranase | 3000 U/ml |
| RM4 enzyme | 200 U/ml |
| Water | balance |
| Total | 100.0% |

Example 11: Troche

| | |
|---|---|
| Gum arabic | 6% |
| Flavor | 0.7 |
| Anethole | 0.5 |
| l-menthol | 0.3 |
| Sodium fluoride | 0.05 |
| Sodium lauroyl sarcosinate | 0.01 |
| Glucose | 36 |
| Palatinose | 36 |
| Dextranase | 4600 U/g |
| RM1 enzyme | 500 U/g |
| Water | balance |
| Total | 100.0% |

Example 12: Chewing gum

| | |
|---|---|
| Gum base | 20% |
| Flavor | 0.7 |
| Anethole | 0.3 |
| l-menthol | 0.3 |
| Sodium fluoride | 0.1 |
| Sodium lauroyl sarcosinate | 0.01 |
| Calcium carbonate | 2 |
| Starch hydrolysate | 15 |
| Powder sugar | 58 |
| Dextranase | 2000 U/g |
| RM1 enzyme | 200 U/g |
| Water | balance |
| Total | 100.0% |

Example 13: Denture cleaner

| | |
|---|---|
| Potassium hydrogen monopersulfate | 35% |
| Sodium perborate | 15 |
| Sodium carbonate | balance |
| Sodium hydrogen carbonate | 25 |
| Citric acid anhydride | 10 |
| Polyethylene glycol | 1 |

-continued

| | |
|---|---|
| Polyvinyl pyrrolidone | 1 |
| Sodium tripolyphosphate | 5 |
| Sodium lauryl sulfate | 1 |
| Dextranase | 6000 U/g |
| RM1 enzyme | 500 U/g |
| Powder flavor | 0.5 |
| Blue No. 1 | trace |
| Total | 100.0% |

Example 14: Denture cleaner

| | |
|---|---|
| Potassium hydrogen monopersulfate | 25% |
| Sodium perborate | 15 |
| Sodium carbonate | balance |
| Sodium hydrogen carbonate | 20 |
| Citric acid anhydride | 10 |
| Crystalline cellulose | 3 |
| Lactose | 2 |
| Polyvinyl pyrrolidone | 2 |
| Sodium tripolyphosphate | 3 |
| Sodium lauryl sulfate | 1 |
| Dextranase | 5000 U/g |
| RM4 enzyme | 1000 U/g |
| Powder flavor | 2 |
| Blue No. 1 | trace |
| Total | 100.0% |

The oral compositions of the present invention have the improved effect of inhibiting plaque formation and mutanase from a specific origin can be blended in oral compositions such as dentifrice in a fully stable manner as commercial products.

What is claimed is:

1. An oral composition comprising mutanase having the following physicochemical properties (1) to (9):

(1) action: an ability to cleave α-1,3-glucosidic links of mutan.
   (2) substrate specificity: an ability to effectively decompose mutan.
   (3) optimum pH: pH 4 to 4.5 when reacting on a mutan substrate at 35° C. for 10 minutes.
   (4) pH range for stability: pH 4 to 10 when kept at 25° C. for 24 hours.
   (5) optimum temperature: 50° to 65° C. when reacted at pH 5 with mutan as a substrate.
   (6) thermal stability: enzyme activity remains stable below 50° C. after incubation at pH 5 for 10 minutes.
   (7) effect of metal ions: mercury and silver show inhibitory effect on a mutan substrate.
   (8) effect of inhibitors: p-chloromercurybenzoic acid shows inhibitory effect on a mutan substrate, and
   (9) molecular weight: about 140,000 to about 160,000 as determined by SDS-polyacrylamide gel electrophoresis.

2. The oral composition of claim 1 further comprising dextranase.

3. The oral composition according to claim 2, which is in a form selected from the group consisting of a dentifrice, a mouth wash, a troche, and a chewing gum.

4. A dentifrice composition according to claim 3, wherein said dentifrice composition further comprises water and at least one ingredient selected from the group consisting of an abrasive, binder, humectant, surfactant, sweetener, preservative and coloring agent.

5. An oral composition according to claim 3, which is a mouth wash composition which further comprises water and at least one ingredient selected from the group consisting of a humectant, sweetener, pH adjusting agent, preservative and solvent.

6. An oral composition according to claim 3, which is a chewing gum.

7. An oral composition according to claim 3, which is a troche.

8. An oral composition according to claim 3, which additionally contains a fluorine compound.

9. An oral composition comprising dextranase and mutanase prepared from a culture which is obtained by cultivating a mutanase-producing microorganism belonging to the genus Bacillus having negative protease producibility, said oral composition comprising mutanase having the following physicochemical properties (1) to (9):

action: an ability to cleave α-1,3-glucosidic links of mutan.
   (2) substrate specificity: an ability to effectively decompose mutan.
   (3) optimum pH: pH 4 to when reacting on a mutan substrate at 35° C. for 10 minutes.
   (4) pH range for stability: pH 4 to 10 when kept at 25° C. for 24 hours.
   (5) optimum temperature: 50° to 65° C. when reacted at pH 5 with mutan as a substrate.
   (6) thermal stability: enzyme activity remains stable below 50° C. after incubation at pH 5 for 10 minutes.
   (7) effect of metal ions: mercury and silver show inhibitory effect on a mutan substrate.
   (8) effect of inhibitors: p-chloromercurybenzoic acid shows inhibitory effect on a mutan substrate, and
   (9) molecular weight: about 140,000 to about 160,000 as determined by SDS-polyacrylamide gel electrophoresis.

* * * * *